(12) United States Patent
Banas et al.

(10) Patent No.: US 6,791,008 B1
(45) Date of Patent: Sep. 14, 2004

(54) USE OF A CLASS OF ENZYMES AND THEIR ENCODING GENES TO INCREASE THE OIL CONTENT IN TRANSGENIC ORGANISMS

(75) Inventors: Antoni Banas, Siedlce (PL); Line Sandager, Copenhagen (DK); Ulf Ståhl, Uppsala (SE); Anders Dahlqvist, Furulund (SE); Marit Lenman, Lund (SE); Hans Ronne, Uppsala (SE); Sten Stymne, Svalöv (SE)

(73) Assignee: Scandinavian Biotechnology Research (ScanBi) AB, Svalov (SE)

( * ) Notice: Subject to any disclaimer, the term of this patent is extended or adjusted under 35 U.S.C. 154(b) by 46 days.

(21) Appl. No.: 09/709,457

(22) Filed: Nov. 13, 2000

Related U.S. Application Data

(60) Provisional application No. 60/164,859, filed on Nov. 12, 1999.

(51) Int. Cl.[7] .......................... A01H 5/00; C12N 15/52; C12N 15/54; C12N 15/81; C12N 15/82
(52) U.S. Cl. .................. 800/281; 800/278; 800/298; 800/306; 536/23.1; 536/23.2; 536/23.7; 435/224; 435/471; 435/483
(58) Field of Search ............................... 435/483, 471, 435/419, 468, 193, 224, 254.11; 800/278, 21, 13, 281, 287, 288, 295, 298, 306, 316, 317, 320; 536/23.1, 23.2, 23.7, 23.74

(56) References Cited

FOREIGN PATENT DOCUMENTS

| WO | WO9745439 | 12/1997 |
|---|---|---|
| WO | WO9855631 | 12/1998 |
| WO | WO9963096 | 12/1999 |

OTHER PUBLICATIONS

Fourgoux–Nicol A. et al. 1999, Plant Molecular Biology 40:857–872.*
Broun P. et al. Science vol. 282 Nov. 13, 1998 pp. 1315–1317.*
Park Y. D. et al., Plant Journal 1996, Feb. 9, (2): 183–194.*
Lardizabal K. et al. WO 98/55631A1 published Dec. 10, 1998.*
Cases et al. *Proc. Natl. Acad. Sci., U.S.A.,* vol. 95, pp. 13018–13023, Oct. 1998.
Cao et al. *Plant Physiol.,* vol. 82, pp. 813–820, 1986.
Meesters et al. *Appl Microbiol Biotechnol,* vol. 45, pp. 575–579, 1996.
Hobbs et al. *Federation of European Biochemical Societies,* Letters452, pp. 145–149, 1999.
Olukoshi et al. *Microbiology,* vol. 140, pp. 931–943, 1994.
Bell et al. *The Enzymes,* vol. XVI, pp. 87–111, 1983.
Lardizabal et al. *1999 Biochemistry and Molecular Biology of Plant Fatty Acids and Glycerolipids Symposium,* Jun. 9–13, 1999, p. 20.
Martin et al. *Triacylglycerol Synthesis in Plants,* pp. 1–6, 1983.
Yang et al. *Science,* vol. 272, pp. 1353–1356, May 31, 1996.
Bligh et al. *Can. J. Biochem. Physiol.,* vol. 37, No. 8, pp. 911–917, Aug. 1959.
Becker et al. *Plant Molecular Biology,* vol. 20, pp. 1195–1198, 1992.
Dahlqvist et al. *PNAS,* vol. 97, No. 12, pp. 6487–6492, Jun. 6, 2000.
Ronne et al. *Molecular and Cellular Biology,* vol. 11, No. 10, pp. 4876–4884, Oct. 1991.
Sherman et al. *Laboratory Course Manual for Methods in Yeast Genetics,* Cold Spring Harbor Laboratory, 1986, pp. 163–167.
Stalberg et al. *Plant Molecular Biology,* vol. 23 pp. 671–683, 1993.
Thomas et al. *Cell,* vol. 56, pp. 619–630, Feb. 24, 1989.
Valvekens et al. *Plant Tissue Culture Manual,* vol. A8, pp. 1–17, 1992.
Yu et al. *The Journal of Biochemistry,* vol. 271, No. 39, pp. 24157–24163, Sep. 27, 1996.
Stahl, *Phospholipases and Transacylases Involved in Triacylglycerol Synthesis,* Presented at 23rd World Congress and Exhibition of the International Society for Fat Research (ISF), Brighton, UK, p. 5, 1999.
Dahqlvist et al. *Enzymes Catalysing a Transacylation Reaction Involved in Triacylglycerol Synthesis,* Presented at Biochem, Mol. Biol. Plant Fatty Acids Glycerolipids Symp., South Lake Tahoe, Jun.9–13, 1999.
Rattray, Microbial Lipids, vol. 1, pp. 555–695, 1988.
Peter Oelkers et al., "Characterization of Two Human Genes Encoding Acyl Coenzyme A: Cholesterol Acyltransferase–related Enzymes*," Journal of Biological Chemistry, US, American Society of Biological Chemists, vol. 273, No. 41, Oct. 1998, pp. 26765–26771.
Douglas H. Hobbs et al., "Cloning of a cDNA encoding diacylglyerol acyltransferase from *Arabidopsis thaliana* and its functional expression." FEBS Letters, NL, Elsevier Science Publishers, Amsterdam, vol. 452, No. 3, Jun. 11, 1999, pp. 145–148.

* cited by examiner

*Primary Examiner*—David T. Fox
*Assistant Examiner*—Russell Kallis
(74) *Attorney, Agent, or Firm*—Young & Thompson

(57) ABSTRACT

The present invention relates to the use of a novel enzyme and its encoding gene for transformation. More specifically, the invention relates to the use of a gene encoding an enzyme with acyl-CoA:diacylglycerol acyltransferase activity. This gene expressed alone in transgenic organisms will increase the total amount of oil (i.e. triacylglycerols) that is produced.

11 Claims, 2 Drawing Sheets

TAG

(35)     (58)

FA

Origin

A      B

SEQUENCE LISTING

<160> NUMBER OF SEQ ID NOS: 2

<210> SEQ ID NO 1
<211> LENGTH: 1833
<212> TYPE: DNA
<213> ORGANISM: Saccharomyces cerevisiae

<400> SEQUENCE: 1

```
atgacggaga ctaaggattt gttgcaagac gaagagtttc ttaagatccg cagactcaat      60
tccgcagaag ccaacaaacg gcattcggtc acgtacgata acgtgatcct gccacaggag     120
tccatggagg tttcgccacg gtcgtctacc acgtcgctgg tggagccagt ggagtcgact     180
gaaggagtgg agtcgactga ggcggaacgt gtggcaggga agcaggagca ggaggaggag     240
taccctgtgg acgcccacat gcaaaagtac ctttcacacc tgaagagcaa gtctcggtcg     300
aggttccacc gaaaggatgc tagcaagtat gtgtcgtttt ttggggacgt gagttttgat     360
cctcgcccca cgctcctgga cagcgccatc aacgtgccct tccagacgac tttcaaaggt     420
ccggtgctgg agaaacagct caaaaattta cagttgacaa agaccaagac caaggccacg     480
gtgaagacta cggtgaagac tacggagaaa acggacaagg cagatgcccc cccaggagaa     540
aaactggagt cgaacttttc agggatctac gtgttcgcat ggatgttctt gggctggata     600
gccatcaggt gctgcacaga ttactatgcg tcgtacggca gtgcatggaa taagctggaa     660
atcgtgcagt acatgacaac ggacttgttc acgatcgcaa tgttggactt ggcaatgttc     720
ctgtgcactt tcttcgtggt tttcgtgcac tggctggtga aaaagcggat catcaactgg     780
aagtggactg ggttcgttgc agtgagcatc ttcgagttgg ctttcatccc cgtgacgttc     840
cccatttacg tctactactt tgatttcaac tgggtcacga gaatcttcct gttcctgcac     900
tccgtggtgt ttgttatgaa gagccactcg tttgcctttt acaacgggta tctttgggac     960
ataaagcagg aactcgagta ctcttccaaa cagttgcaaa aatacaagga atctttgtcc    1020
ccagagaccc gcgagattct gcaaaaaagt tgcgactttt gccttttcga attgaactac    1080
cagaccaagg ataacgactt ccccaacaac atcagttgca gcaatttctt catgttctgt    1140 ttgttcccg tcctcgtgta ccagatcaac tacccaagaa cgtcgcgcat cagatggagg    1200
tatgtgttgg agaaggtgtg cgccatcatt ggcaccatct tcctcatgat ggtcacggca    1260
cagttcttca tgcacccggt ggccatgcgc tgtatccagt tccacaacac gcccaccttc    1320
ggcggctgga tccccgccac gcaagagtgg ttccacctgc tcttcgacat gattccgggc    1380
ttcactgttc tgtacatgct cacgttttac atgatatggg acgctttatt gaattgcgtg    1440
gcggagttga ccaggtttgc ggacagatat ttctacggcg actggtggaa ttgcgtttcg    1500
tttgaagagt ttagcagaat ctggaacgtc cccgttcaca aatttttact aagacacgtg    1560
```

-continued

```
taccacagct ccatgggcgc attgcatttg agcaagagcc aagctacatt atttactttt      1620
ttcttgagtg ccgtgttcca cgaaatggcc atgttcgcca ttttcagaag ggttagagga      1680
tatctgttca tgttccaact gtcgcagttt gtgtggactg ctttgagcaa caccaagttt      1740
ctacgggcaa gaccgcagtt gtccaacgtt gtcttttcgt ttggtgtctg ttcagggccc      1800
agtatcatta tgacgttgta cctgacctta tga                                   1833
```

<210> SEQ ID NO 2
<211> LENGTH: 610
<212> TYPE: PRT
<213> ORGANISM: Saccharomyces cerevisiae

<400> SEQUENCE: 2

```
Met Thr Glu Thr Lys Asp Leu Leu Gln Asp Glu Phe Leu Lys Ile
 1               5                  10                  15

Arg Arg Leu Asn Ser Ala Glu Ala Asn Lys Arg His Ser Val Thr Tyr
                20                  25                  30

Asp Asn Val Ile Leu Pro Gln Glu Ser Met Glu Val Ser Pro Arg Ser
            35                  40                  45

Ser Thr Thr Ser Leu Val Glu Pro Val Glu Ser Thr Glu Gly Val Glu
        50                  55                  60

Ser Thr Glu Ala Glu Arg Val Ala Gly Lys Gln Glu Gln Glu Glu Glu
    65                  70                  75                  80

Tyr Pro Val Asp Ala His Met Gln Lys Tyr Leu Ser His Leu Lys Ser
                85                  90                  95

Lys Ser Arg Ser Arg Phe His Arg Lys Asp Ala Ser Lys Tyr Val Ser
               100                 105                 110

Phe Phe Gly Asp Val Ser Phe Asp Pro Arg Pro Thr Leu Leu Asp Ser
           115                 120                 125

Ala Ile Asn Val Pro Phe Gln Thr Thr Phe Lys Gly Pro Val Leu Glu
       130                 135                 140

Lys Gln Leu Lys Asn Leu Gln Leu Thr Lys Thr Lys Thr Lys Ala Thr
145                 150                 155                 160

Val Lys Thr Thr Val Lys Thr Thr Glu Lys Thr Asp Lys Ala Asp Ala
                165                 170                 175

Pro Pro Gly Glu Lys Leu Glu Ser Asn Phe Ser Gly Ile Tyr Val Phe
            180                 185                 190

Ala Trp Met Phe Leu Gly Trp Ile Ala Ile Arg Cys Cys Thr Asp Tyr
        195                 200                 205

Tyr Ala Ser Tyr Gly Ser Ala Trp Asn Lys Leu Glu Ile Val Gln Tyr
    210                 215                 220

Met Thr Thr Asp Leu Phe Thr Ile Ala Met Leu Asp Leu Ala Met Phe
225                 230                 235                 240

Leu Cys Thr Phe Phe Val Val Phe Val His Trp Leu Val Lys Lys Arg
                245                 250                 255

Ile Ile Asn Trp Lys Trp Thr Gly Phe Val Ala Val Ser Ile Phe Glu
            260                 265                 270

Leu Ala Phe Ile Pro Val Thr Phe Pro Ile Tyr Val Tyr Tyr Phe Asp
        275                 280                 285

Phe Asn Trp Val Thr Arg Ile Phe Leu Phe Leu His Ser Val Val Phe
    290                 295                 300

Val Met Lys Ser His Ser Phe Ala Phe Tyr Asn Gly Tyr Leu Trp Asp
305                 310                 315                 320
```

-continued

```
Ile Lys Gln Glu Leu Glu Tyr Ser Ser Lys Gln Leu Gln Lys Tyr Lys
                325                 330                 335

Glu Ser Leu Ser Pro Glu Thr Arg Glu Ile Leu Gln Lys Ser Cys Asp
                340                 345                 350

Phe Cys Leu Phe Glu Leu Asn Tyr Gln Thr Lys Asp Asn Asp Phe Pro
                355                 360                 365

Asn Asn Ile Ser Cys Ser Asn Phe Phe Met Phe Cys Leu Phe Pro Val
        370                 375                 380

Leu Val Tyr Gln Ile Asn Tyr Pro Arg Thr Ser Arg Ile Arg Trp Arg
385                 390                 395                 400

Tyr Val Leu Glu Lys Val Cys Ala Ile Ile Gly Thr Ile Phe Leu Met
                405                 410                 415

Met Val Thr Ala Gln Phe Phe Met His Pro Val Ala Met Arg Cys Ile
                420                 425                 430

Gln Phe His Asn Thr Pro Thr Phe Gly Gly Trp Ile Pro Ala Thr Gln
                435                 440                 445

Glu Trp Phe His Leu Leu Phe Asp Met Ile Pro Gly Phe Thr Val Leu
        450                 455                 460

Tyr Met Leu Thr Phe Tyr Met Ile Trp Asp Ala Leu Leu Asn Cys Val
465                 470                 475                 480

Ala Glu Leu Thr Arg Phe Ala Asp Arg Tyr Phe Tyr Gly Asp Trp Trp
                485                 490                 495

Asn Cys Val Ser Phe Glu Glu Phe Ser Arg Ile Trp Asn Val Pro Val
                500                 505                 510

His Lys Phe Leu Leu Arg His Val Tyr His Ser Ser Met Gly Ala Leu
                515                 520                 525

His Leu Ser Lys Ser Gln Ala Thr Leu Phe Thr Phe Phe Leu Ser Ala
        530                 535                 540

Val Phe His Glu Met Ala Met Phe Ala Ile Phe Arg Arg Val Arg Gly
545                 550                 555                 560

Tyr Leu Phe Met Phe Gln Leu Ser Gln Phe Val Trp Thr Ala Leu Ser
                565                 570                 575

Asn Thr Lys Phe Leu Arg Ala Arg Pro Gln Leu Ser Asn Val Val Phe
                580                 585                 590

Ser Phe Gly Val Cys Ser Gly Pro Ser Ile Ile Met Thr Leu Tyr Leu
                595                 600                 605

Thr Leu
    610
```

USE OF A CLASS OF ENZYMES AND THEIR ENCODING GENES TO INCREASE THE OIL CONTENT IN TRANSGENIC ORGANISMS

This application claims the benefit of U.S. Provisional Application No. 60/164,859 filed Nov. 12, 1999. should appear as the first sentence of the description.

FIELD OF THE INVENTION

The present invention relates to the use of a novel enzyme and its encoding gene for transformation. More specifically, the invention relates to the use of a gene encoding an enzyme with acyl-CoA : diacylglycerol acyltransferase activity. This gene expressed alone in transgenic organisms will increase the total amount of oil (i.e. triacylglycerols) that is produced.

BACKGROUND OF THE INVENTION

In oil crops like rape, sunflower, oilpalm etc., the oil (i.e. triacylglycerols) is the most valuable product of the seeds or fruits and other compounds such as starch, protein and fiber is regarded as by-products with less value. Enhancing the quantity of oil per weight basis at the expense of other compounds in oil crops would therefore increase the value of the crop. If enzymes regulating the allocation of reduced carbon into the production of oil can be upregulated by overexpression, the cells will accumulate more oil at the expense of other products. This approach could not only be used to increase the oil content in already high oil producing organisms such as oil crops, they could also lead to significant oil production in moderate or low oil containing crops such as soy, oat, maize, potato, sugar beats, and turnips as well as in microorganisms.

Development in genetic engineering technologies combined with greater understanding of the biosynthesis of triacylglycerols now makes it possible to transfer genes coding for key enzymes involved in the synthesis of triacylglycerols from a wild plant species or organisms of other kingdoms into domesticated oilseed crops. In this way, triacylglycerols can be produced in high purity and quantities at moderate costs.

It is known that the biosynthesis of triacylglycerols (TAG) in fat-accumulating tissues in animals (Bell & Coleman, 1983) and plants (Cao & Huang, 1986, Martin & Wilson 1983) as well as the accumulation of oil in microbial organisms such as bacteria (Ekundayo & Packler, 1994), yeast and other fungi (Ratledge 1989) can be catalyzed by acyl-CoA : diacylglycerol acyltransferases (DAGATs), enzymes that transfer an acyl-group from acyl-CoA to diacylglycerol, thus forming TAG.

During the past few years genes coding for DAGATs, have been identified in animals (Cases et al., 1998), plants (Hobbs et al., 1999; Lardizabal et al., 2000) and in microbes (Lardizabal et al., 1999). These DAGATs belong to two unrelated protein families.

The first type of DAGAT that was characterized, DAGAT A, has so far been found only in animals (Cases et al., 1998) and plants (Hobbs et al. 1999). These genes show sequence similarities to genes encoding acyl-CoA : cholesterol acyl-transferase (ACAT). The mouse DAGAT A has 20% amino acid sequence identity to the mouse ACAT (Cases et al., 1998). However, DAGATs A from plants and animals are more similar to each other than to ACAT. Thus, the mouse DAGAT A has 38% amino acid sequence identity to the *Arabidopsis thaliana* DAGAT A (Hobbs et al., 1999). It is also approximately 80% identical to the human ACAT like protein ARGP1, which was suggested to be involved in TAG synthesis (Oelkers et al., 1998), indicating that ARGP1 is a DAGAT A.

The yeast *S. cerevisiae* contain 2 genes with sequence similarity to ACAT, ARE1 and ARE2 (Yang et al., 1996). The encoded proteins have approximately 24% overall amino acid sequence identity to the mouse ACAT and 15% identity to the DAGAT A from mouse. It should be noted that they are both more similar to each other (45% amino acid sequence identity) than to either ACATs or DAGATs from higher eukaryotes. It is not possible to classify them as putative ACATs or DAGATs based on sequence similarities alone, since their evolutionary distances from both groups of higher eukaryotic enzymes are similar. However, experiments have shown that both Are1 and Are2 are ACATs, which together are responsible for all of the sterol ester synthesis that occurs in yeast (Yang et al., 1996; Yu et al., 1996). The possible involvement of Are1 and Are2 in the synthesis of TAG has also been studied (Yang et al., 1996; Yu et al., 1996). From these studies, it was concluded that Are1 and Are2 are not involved in TAG synthesis. Thus, these is no prior art to show that Are1 is a TAG synthesizing enzyme, nor can it be concluded, on the basis of homologies to ACAT like sequences already published, that Are1 is a DAGAT (Lassner and Ruezinsky, 1999).

The second family of DAGAT enzymes, the DAGAT B family, is unrelated to any other known proteins. These enzymes show no sequence homology to the mouse and plant ACAT like DAGAT A proteins (Lardizabal et al., 2000) or to any other known proteins.

DAGAT A and B are not the only enzymes that contribute to TAG biosynthesis. TAG can also be synthesized by an acyl-CoA independent reaction. Thus, the newly discovered enzyme phospholipid : diacylglycerol acyltransferase (PDAT) catalyses the formation of TAG by transferring an acryl group from the sn-2 position of a phospholipid to DAG (Dahlqvist et al., 1999; Ståhl, 1999).

SUMMARY OF INVENTION

This invention describes the identification of a gene encoding an enzyme that is partly responsible for TAG accumulation in yeast.

In a first embodiment, this invention is directed to the TAG synthesising enzyme comprising an amino acid sequence as set forth in SEQ ID NO 2 or a functional fragment, derivative, variant, ortologue or isoenzyme thereof.

The present invention further includes the nucleotide sequence as set forth in SEQ ID NO 1, as well as portions of the genomic sequence, the cDNA sequence, allelic variants, synthetic variants and mutants thereof. This includes sequences that codes for variants of the polypeptide set forth in the sequence listing including biologically active triacylglycerol synthesising enzymes as well as sequences that are to be used as probes, vectors for transformation or cloning intermediates.

Another aspect of the present invention relates to hose polypeptides, which have at least 60% identity to SEQ ID NO 2. Preferred embodiments are polynucleotides that encode polypeptides with diacrylglycerol acyltransferase activity.

In a different aspect, this invention relates to the use of these nucleotide sequences in recombinant DNA constructs to direct the transcription and translation of the diacylglycerol acyltransferase sequence of the present invention in a host organisms or progeny thereof, including oil seeds, yeast and other fungi, as well as other oil accumulating organisms.

Cells and organisms containing the diacylglycerol acyltransferase as a result of the production of the acyltransferase encoding sequence are also included within the scope of the invention.

Of particular interest is the expression of the nucleotide sequences of the present invention from transcription initiation regions that are preferentially expressed in plant seed tissues. It is contemplated that the gene sequence may be synthesized, especially when there is interest to provide plant-preferred codons.

In a different embodiment, this invention also relates to methods of using a DNA sequence encoding a said protein of the present invention for increasing the oil-content within the cells of different organisms.

Further, the invention makes possible a process for the production of triacylglycerol, which comprises growing transgenic cells or organisms under conditions whereby any of the nucleotide sequences discussed above are expressed in order to produce an enzyme in these cells with the ability to transfer a fatty acid from acyl-CoA to diacylglycerol, thus forming triacylglycerol.

Moreover, triacylglycerols produced by the aforementioned process are included in the scope of the present invention.

The present invention can be essentially characterized by the following aspects:

1. Use of a nucleic acid sequence encoding an enzyme catalysing the transfer of a fatty acid from acyl-CoA to diacylglycerol for the production of triacylglycerol (TAG) by genetic transformation of an oil-producing organism with said sequence in order to be expressed in this organism and result in an active enzyme in order to increase the oil content of the organism.

The nucleic acid sequence is derived from the sequence shown in SEQ ID NO. 1, from the *Saccharomyces cerevisiae* ARE1 gene (genomic clone or cDNA), or from a nucleic acid sequence or cDNA that contain nucleotide sequences coding for a protein with an amino acid sequence that is 60% or more identical to the amino acid sequence as presented in SEQ. ID. NO. 2.

2. Transgenic organisms comprising, in their genome or on a plasmid, a nucleic acid sequence according to the above, transferred by recombinant DNA technology. The transgenic organisms are selected from the group consisting of fungi, plants and animals. Preferably the transgenic organisms agricultural plants and preferably said nucleotide sequence is expressed under the control of a storage organ specific promoter. Alternatively, the nucleotide, the nucleotide sequence is expressed under the control of a seed-specific promoter.

3. Oils from organism according to aspect 2.

4. A protein encoded by a DNA molecule according to SEQ ID NO. 1 or a functional (enzymatically active) fragment thereof. Alternatively, the protein produced in an organism as specified in aspect 2, which has the amino acid sequence set forth in SEQ ID NO. 2 or an amino acid sequence with at least 60% homology to said amino acid sequence. Preferably the protein is isolated from *Saccharomyces cerevisiae*.

5. Use of a protein as specified in aspect 4 in the production of triacylglycerols.

6. Triacylglycerols according to aspect 5.

DETAILED DESCRIPTION OF THE INVENTION

The invention now having generally described will be more readily understood by reference to the following drawings and examples, which are included for the purpose of illustration only, and are not intended to limit scope of the present invention.

Figure 1:
FIG. 1. In vitro DAGAT activity in a yeast strain (SCY62) that overexpresses the ARE1 gene. Aliquots of microsomal membranes prepared from the control strain (lane A) or the ARE1 overexpressing strain (lane B) were assayed for DAGAT activity according to Method A described in Material and Methods. The radioactive triacylglycerol synthesised was visualised and quantified as cpm (figures in brackets) on the TLC plate by electronic autoradiography (Instant Imager, Packard, US). Abbreviations used in the figure: triacylglycerol (TAG) and unesterified fatty acids (FA).
Figure 1:
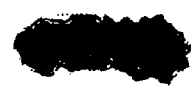

The radioactive triacylglycerols (TAG) synthesized in microsomes from the double mutant, H1226 (lane A), the triple mutant, H1236 (lane B) and the same triple mutant containing a plasmid that overexpresses the ARE1 gene (lane C) were visualised in a TLC plate by electronic autoradiography (Instant Imager, Packard, US).

BRIEF DESCRIPTION OF THE SEQ ID:

SEQ ID NO. 1: Genomic DNA sequence of the *Saccharomyces cerevisiae* ARE1 gene, ORF YCR048W.

SEQ ID NO. 2: The amino acid sequence of the open reading frame YCR048W from *Saccharomyces cerevisiae*.

EXAMPLES

Example 1

Triacylglycerol accumulation is reduced in yeast cells that lack the ARE1 gene.

Materials and Methods

Yeast strains. Yeast strains used in this study were congenic to the W303-1A (Thomas & Rothstein, 1989) background. An are1 mutant strain, H1111, with the genotype MATα are1-Δ::HIS3 ADE2 can 1-100 leu2-3, 112 trip1-1 ura3-1, was generated by crossing the two strains SCY60 (MATα are1-Δ::HIS3 ade2-1 can 1-100 leu2-3, 112 trp1-1 ura3-1) and SCY61 (MATα are2-Δ::LEU2 ADE2 can 1-100 his3-11,15 trp1-1 ura3-1) (Yang et al., 1996) and dissecting tetrads. As a wild type control, we used SCY62 (MATα ADE2 can 1-100 his3-11,15 leu2-3 trp1-1 ura3-1) (Yang et al., 1996). Yeast mutant strains disrupted in YNR008w and YOR245c encoding yeast DAGAT B and PDAT, respectively, and the ARE1 gene were constructed through a series of yeast transformations using the lithium acetate method. Linear DNA fragments used for the disruption of the YOR245c and YNR008w genes were created as follows. Printers specific for YOR245c (300 bases upstream, CAGCATTGACGTAATGGGAA, and downstream, AAAGCCAAAAAGAGAAGGACA, of the gene) were constructed and the gene was synthesised using PCR from SCY62 genomic DNA. The PCR-fragment was blunt-ended and ligated into pUC119 previously cleaved with the restriction enzyme SmaI. The resulting plasmid, YOR245c-pUC119, was then digested with ClaI/StuI and dephosphorylated to prevent religation. The marker KanMX4 was obtained by digestion of the plasmid pFA6a by SmaI/SacI. The blunted KanMX4 fragment was then ligated into the YOR245c-pUC119 vector between the ClaI and SluI sites within the YOR245c open reading frame. A linear fragment containing the resulting YOR245c::KanMX4 disruption cassette was finally obtained through cleavage by BamHI/NdeI. The linear fragment used to disrupt the YNR008w gene was constructed in a similar manner as the YOR245c::KanMX4 fragment. The YNR008w gene was constructed in a similar manner as the YOR245c::KanMX4 fragment. The YNR008w gene was amplified from SCY62 genomic DNA, cloned into the pBluescript vector (Dahlqvist et al., 2000) and digested with restriction enzyme BbsI/MunI. The TRP1 marker was then ligated between the BbsI and MunI sites in the YNR008w-pBluescript plasmid, and a linear fragment containing the disruption cassette was obtained by BamHI/PstI digestion. The single PDAT mutant, H1079, with the genotype MATa pdat-Δ::TRP1 ADE2 leu2-3, 112 ura3-1 his-3-11,15 trip1-1, was generated by transforming the wild type strain SCY62 with the linear YNR008w::TRP1 fragment. The PDAT DAGAT B double mutant, H1226, with the genotype MATa pdat-Δ::TRP1 dagat B-Δ::KanMX4 ADE2 leu2-3,112 ura3-1 his3-11,15 trp1-1, was constructed in an identical manner by transforming H1079 with the linear YOR245c::KanMX4 fragment. An ARE1 PDAT double mutant, H1224, with the genotype MATα are1-Δ::TRP1 ADE2 can 1-100 leu2-3,112 ura3-1 trp1-1, was generated by transforming Il1111 with the linear YNR008w::TRP1 fragment. The triple mutant strain, H1236, with the genotype MATα are1-Δ::HIS3 pdat-Δ::TRP1 dagat B-Δ::KanMX4 ADE2 leu2-3, 112 ura3-1 trp-1-1, was constructed by transforming Il1224 with the linear YOR245c::KanMX4 fragment. Yeast Cultivations. Yeast cells were cultivated at 28 or 30° C. on a rotary shaker in liquid YPD medium (1% yeast extract, 2% peptone, 2% glucose). Transformed cells were grown in synthetic medium (Sherman et al., 1986) lacking uracil and supplemented with 2% (vol/vol) glycerol and 2% (vol/vol) ethanol.

Lipid Analysis. The lipid content of the yeast cells was determined as described by Dahlqvist et al. (2000) and is presented as nmol of fatty acid (FA) per mg dry weight yeast.

Results

The lipid content of a mutant yeast strain (SCY60), in which the ARE1 gene was disrupted, was analyzed and compared to wild type yeast cells (SCY62) at different stages of growth. In are1 mutant cells, harvested in exponential phase after 10 hours of cultivation, the total amount of lipid, measured as nmol FA per dry weight yeast, was not significantly different from the wild type yeast (table 1), nor did the amount of fatty acids accumulated into TAG differ strongly between the wild-type and the are1 mutant. The effect of the are1 disruption on oil accumulation in stationary phase cells was analysed in an experiment were the yeast cells were pre-cultivated for 24 h in liquid YPD medium. The cells were then harvested and re-suspended in minimal medium (Meesters et al., 1996), supplemented with 16 g/l glycerol, to the original volume of the growth culture. In this glycerol supplemented minimal medium the yeast cells will enter stationary phase under conditions suitable for TAG accumulation. After further cultivation for 24 h, the cells were harvested and their lipid composition was determined. The total lipid content in the are1 mutant was 15% less than in the wild type. The TAG amount in the are1 mutant was almost 40% lower than in the wild type, whereas the polar lipid content did not differ significantly between the are1 mutant and the wild type yeast (table 1).

Two other genes, YNR008w and YOR254c (Ståhl, 1999; Dahlqvist, et al., 2000; Lardizabal et al., 2000) have recently been shown to be involved in TAG synthesis in yeast. These genes encode a PDAT and a DAGAT B protein, respectively. A yeast strain disrupted in all three genes (ARE1, YNR008w and YOR254c) and a yeast strain with disruptions in only the PDAT and DAGAT B genes were made and they are here named the tripe and double mutant, respectively. The TAG content of the double mutant was 48% of the wild type (table 2), whereas the amount of TAG accumulated in the triple mutant was only 4% of the level in the wild type yeast. By comparing the amounts of TAG accumulated in the double triple mutants it is clear that Are1 protein contributes to TAG synthesis in yeast.

In summary, these experiment clearly show that the product of the ARE1 gene contributes to TAG accumulation in yeast.

TABLE 1

Lipid content in ARE1 mutant (SCY60) and wild type (SCY62) yeast cells. The lipid accumulation in yeast disrupted in the ARE1 gene (are1 mutant) was analysed at different stages of growth and compared to the control wild type yeast. The lipid composition of cells in exponential growth was analysed after 10 hours of cultivation in YPD medium at 28° C. Yeast cells in stationary phase was prepared by pre-cultivating the cells on liquid YPD medium for 24 hours at 28° C., after which the cells were harvested, re-suspended in minimal medium (Meesters et al, 1996) supplemented with 16 g/l glycerol, and cultivated for an additional 24 hours at 28° C. The content of sterol esters, TAG, other neutral lipids, and polar lipids was determined as nmol fatty acids (FA) per mg of dry yeast weight.

|  | SCY62 (nmol FA/mg) | | SCY60 (nmol FA/mg) | |
| --- | --- | --- | --- | --- |
|  | 10 h | 48 h | 10 h | 48 h |
| Sterol esters | 15 | 24 | 12 | 19 |
| Triacylglycerol | 6 | 44 | 8 | 28 |
| Other neutral lipids | 4 | 6 | 4 | 5 |
| Polar lipids | 65 | 74 | 63 | 74 |
| Total lipids | 90 | 148 | 87 | 126 |

TABLE 2

Lipid content in the PDAT DAGATB double mutant strain (H1226), if the PDAT DAGATB ARE1 triple mutant strain (Il1236) and in wild type yeast cells (SCY62). The different yeast stains, all of which contained the empty expression plasmid pJN92 (Ronne et al., 1991), were cultivated in YNB medium to which 2% (v/v) of galactose was added at an $A_{600}$ of 4. The cells were harvested after an additional 22 hours growth and the content of sterol esters, TAG, other neutral lipids, and polar lipids was determined as nmol fatty acids (FA) per mg of dry yeast weight.

|  | SCY62 (nmol FA/mg) | H1226 (nmol FA/mg) | Il1236 (nmol FA/mg) |
| --- | --- | --- | --- |
| Sterol esters | 13 | 10 | 1 |
| Triacylglycerol | 163 | 78 | 7 |
| Other neutral lipids | 17 | 16 | 41 |
| Polar lipids | 58 | 66 | 44 |
| Total lipids | 251 | 170 | 87 |

Example 2

Triacylglycerol accumulation is increased in yeast cells that overexpress the ARE1 gene.

Material and Methods

For induced overexpression of the ARE1 gene, a 2001 bp EheI/Ecl136II fragment from the plasmid YEP 3-16 (Yang et al., 1996) was cloned into the BamHI site of the GAL1 expression vector pHN92 (Ronne et al., 1991), thus generating pUS5. The wild type yeast strain SCY62 (MATα ADE2 can 1-100 his3-11,15 leu2-3 trp1-1 ura3-1) (Yang et al., 1996), was transformed with the pUS5 and cultivated at 28° C. on a rotary shaker in synthetic medium (Sherman et al., 1986) lacking uracil and supplemented with 2% (vol/vol) glycerol and 2% (vol/vol) ethanol. The GAL1 promoter was induced after 43 h of growth by the addition of 2% (wt/vol) final concentration of galactose. Cells were harvested after an additional 24 hours of growth. Wild type (SCY62) cells transformed with the empty vector, pJN92, and cultivated under identical conditions were used as a control. The lipid content of the yeast cells was determined as described by Dahlqvist et al. (2000) and is presented as nmol of fatty acid (FA) per mg dry weight yeast.

Results

The effect of overexpression of the ARE1 gene on lipid accumulation was studied by transforming the wild-type yeast (strain SCY62) with a plasmid containing the ARE1 gene under control of the galactose-induced GAL1 promoter (Table 3). Overexpression of the ARE1 gene from this promoter had no strong effect on the growth rate as determined by optical density measurements. However, the total lipid content in yeast cells that overexpressed ARE1 was 1.4 fold higher than in the control yeast transformed with an empty expression vector (Table 3). The elevated lipid content in yeast cells overexpressing ARE1 is mostly due to a 50% increase in the TAG content, but the amount of sterol esters also increased significantly in these cells, as compared to the control. These results clearly demonstrate that the gene product of ARE1, in addition to its earlier reported involvement in the synthesis of sterol esters (Yang et al., 1996), also is involved in TAG synthesis. The elevated levels of TAG achieved in the ARE1 overexpressing cells also clearly demonstrate the potential use of the ARE1 gene in increasing the oil content in transgenic organisms.

TABLE 3

Lipid content in yeast cells that overexpress the ARE1 gene. Yeast cells (SCY62) transformed with the ARE1 gene under the control of the GAL1 promotor in the pJN92 vector were cultivated as described in the Material and Method section. Yeast cells (SCY62), transformed with an empty vector, cultivated under identical conditions were used as control. The cells were harvested and the content of sterol esters, triacylglycerols, other neutral lipids and polar lipids was determined as nmol fatty acids (FA) per mg dry yeast weight.

|  | SCY62 (nmol FA/mg) | SCY62 overexpressing ARE1 (nmol FA/mg) |
| --- | --- | --- |
| Sterol esters | 19 | 27 |
| Triacylglycerol | 160 | 239 |
| Other neutral lipids | 30 | 32 |
| Polar lipids | 48 | 56 |
| Total lipids | 257 | 354 |

Example 3

The ARE1 gene product has diacylglycerol acyltransferase activity.

Materials and Methods

In vitro diacylglycerol acyltransferase (DAGAT) activity was analyzed, in microsomal fractions prepared from yeast cells, by using one of the following methods.

Method A: A wild type yeast (strain SCY62) was transformed with a plasmid (pUS5) containing the ARE1 gene under the control of a GAL1 promoter (described in Material and Methods in Example 2). The transformed yeast was cultivated at 28° C. in defined YNB medium lacking uracil. The expression of the ARE1 gene was induced by the addition of 2% (v/v) galactose after 8 hours growth and the cells were harvested after an additional 17 hours. Microsomal membranes were prepared from the transformed yeast by resuspending 1 g of yeast (fresh weight) in 8 ml of ice-cold buffer (20 mM Tri-Cl, pH 7.9, 10 mM $MgCl_2$, 1 mM EDTA, 5% (v/v) glycerol, 1 mM DTT, 0.3 M ammonium sulphate) in a 12 ml glass tube to which 4 ml of glass bends (diameter 0.45–0.5 mm) were added. The glass tube was heavily shaken (3×60 s) with a MSK cell homogenizer (B. Braun Melsungen AG, Germany). The suspension was centrifuged at 20 000 g for 15 min at 6° C. and the resulting supernatant was centrifuged at 100 000 g for 2 h at 6° C. The resulting pellet, containing microsomal membranes, was resuspended in 0.1 M K-phosphate (pH 7.2) buffer and stored at −80° C. DAGAT activity was analyzed in aliquots of microsomal membranes (50 $\mu$l), corresponding to 10 nmol phosphatidylcholine, to which 1 $\mu$mol of dioleoyl-PG and 0.25 $\mu$mol of dioleoyl-DAG emulsified in 50 $\mu$l of buffer containing 190 mM HEPES-NaOH, pH 7.5, 125 mM $MgCl_2$, 30 mM CHAPS, 2.5 mg/ml BSA and 2 nmol [$^{14}$C]-palmitoyl-CoA (2775 dpm/nmol), were added. The reaction mixture was incubated at 30° C. for 30 min. The lipids were then extracted in chloroform and separated using thin layer chromatography on silica gel 60 plates in hexane/diethyl ether/acetic acid (80:20:1). The radioactive lipids were visualized and quantified on the plates by electronic autoradiography (Instant Imager, Packard, US).

Method B: The PDAT DAGAT B double mutant (H1226) and the PDAT DAGAT B ARE1 triple mutant (II1236), described in Material and Methods in Example 1, were transformed with the empty expression plasmid (pJN92). A transformant expressing the ARE1 gene under the control of the GAL1 promoter was generated by transforming the triple mutant H1236 with the plasmid pUS5 (described in Material and Methods in Example 2). All yeast transformants were cultivated in YNB medium to which 2% (v/v) of galactose was added at an $A_{600}$ of 4. The cells were harvested after an additional 6 hours growth and microsomes were prepared using a modification of the procedure of Dahlqvist et al. (2000). Yeast cells (0.2 g) were resuspended in 1.5 ml of ice-cold buffer (20 mM Tris-Cl pH 7.9, 10 mM $MgCl_2$, 1 mM EDTA, 5% (vol/vol) glycerol, 1 mM DTT, 0.3 M ammonium sulfate) in a 2 ml Eppendorf tube containing 0.2 ml glass beads (0.45–0.5 mm in diameter). The tube was heavily shaken (3×60 s) in a cell homogenizer (Mini Bead Beater). The homogenized yeast was centrifuged at 1350×g for 20 min at 4° C., and the resulting supernatant was subsequently centrifuged at 150 000×g for 1 h at 4° C. The pellet was re-suspended in 0.1 M potassium phosphate (pH 7.2), and stored at −80° C. Dihexanoyl-DAG (5 nmol) dissolved in chloroform was added to micro tubes and the chloroform was evaporated under a stream of $N_2$. Aliquots (90 $\mu$l) of microsomal fractions corresponding to 150 $\mu$g protein, in a buffer consisting of 50 mM HEPES (pH 7.2), 5 mM $MgCl_2$, and 1 mg/ml BSA were added to the tubes and the suspension was thoroughly mixed. Finally, 10 $\mu$l of [$^{14}$C]-palmitoyl-CoA (20 nmol, 5000 dpm/nmol) was added, and the mixtures were incubated at 30° C. for 15 min. Lipids were extracted from the reaction mixture into chloroform (Bligh & Dyer, 1959) and separated by TLC on silica gel 60 plates (Merck). The TLC plate was first developed in chloroform/methanol/acetic acid/water (85:15:10:3.5) for 80 mm. The dried plate was then developed in hexane/diethyl ether/acetic acid (80:20:1.5) for 180 mm. The radioactive lipids were visualized and quantified on the plates by electronic autoradiography (Instant Imager, Packard).

Results

Figure 2:
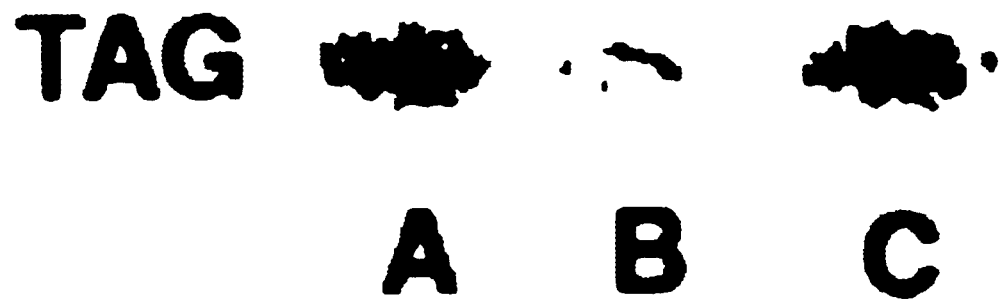
FIG. 2. In vitro DAGAT activity in a PDAT DAGAT B double mutant, a PDAT DAGAT B ARE1 triple mutant, and in the same triple mutant containing a plasmid that overexpresses the ARE1 gene.

Microsomal membranes prepared from the transformed yeast overexpressing the ARE1 gene and from control yeast transformed with an empty plasmid (pJN92) were assayed for DAGAT activity according to Method A in Materials and Methods. The amount of radiolabelled TAG synthesized from [$^{14}$C]palmitoyl-CoA in microsomal membranes prepared from the ARE1 overexpressor was increased with 66% as compared to the control yeast (FIG. 1). DAGAT activity was also assayed in microsomal membranes prepared from the PDAT DAGAT B double mutant strain (H1226) and the PDAT DAGAT B ARE1 triple mutant strain (H1236) cells (method B). In the double mutant, with a functional ARE1 gene, TAG with two hexanoyl and one [$^{14}$C]palmitoyl chain, was synthesized from added dihexanoyl-DAG and [$^{14}$C] palmitoyl-CoA. This synthesis was barely detectable in the triple mutant (FIG. 2) where the ARE1 gene was disrupted. However, the in vitro synthesis of TAG was restored in triple mutant cells transformed with a plasmid expressing the ARE1 gene. This clearly shows that the in vitro synthesis of TAG in these yeast mutants correlates with the presence of a functional ARE1 gene and that the protein encoded by the ARE1 gene possesses DAGAT activity.

Example 4

Triacylglycerol accumulation is increased in the seeds of Arabidopsis thaliana that express the ARE1 gene.

Material and Methods

The ARE1 gene was amplified from the yeast genome using the proof reading enzyme polymerase pfu (Promega). An EcoR1 and Xba1 restriction enzyme site was introduced respectively into the 5' and 3' ends of this fragment to allow directional cloning of the fragment. The PCR fragment was cloned into the vector pBluescript (Stratagene). The insert derived from this plasmid was then cloned downstream of a napin promoter fragment (Stålberg et al., 1993) in the vector pPGTV-KAN (Becker et al., 1993). This plasmid was transformed into Agrobacterium strain GV3301. Transformed Agrobacterium cells were then used to transform root explants from Arabidopsis thaliana (Valvekens et al., 1992). The lipid content in Arabidopsis seeds was determined by methylation of fatty acids. Fatty acids in the oil of proximately 2–3 mg of seeds were methylated in 2 ml 2% (vol/vol) H$_2$SO$_4$ in dry methanol for 90 min at 90° C. The fatty acid method esters were extracted with hexane and analyzed by GLC through a 50 m×0.32 mm CP-Wax58-CB fused-silica column (chrompack), methylheptadecanoic acid was used as internal standard.

Results

A. thaliana was transformed with the ARE1 gene under the control of a napin promoter, which is seed specific and active during the major phase of oil accumulation. The oil content was analyzed in seeds from single T2 plants derived from four independent transformation events (Table 4). The results showed that in three lines between 50% and 100% of the T2 plants generated seeds with statistically significant elevated oil content as compared to the oil content in the seeds from the control plants. The oil content was elevated with up to 18% in the seeds expressing ARE1. One line (28-1) had the same oil content as the seeds from the control plants.

TABLE 4

Accumulation of oil in seeds from Arabidopsis thaliana transformed with the ARE1 gene.
T2 plants transformed with the ARE1 gene under the control of the napin promotor and control plants transformed with an empty vector were cultivated in a growth chamber under controlled conditions. The oil content in mature seeds of these plants was determined by GLC analyses and is presented as nmol fatty acids (FA) per mg seed.

| | Transformants | | | | |
|---|---|---|---|---|---|
| | control | 28-1 | 28-2 | 28-3 | 28-4 |
| Number of T2 plants analyzed | 4 | 6 | 2 | 6 | 11 |
| Number of T2 plants with significant increased seed oil content* | — | 0 | 2 | 3 | 9 |
| nmol FA per mg seed in T2 plant with highest oil content | 1535 ± 114 | 1562 ± 28 | 1753 ± 53 | 1641 ± 82 | 1818 ± 18 |

*Calculated with the mean difference two-sided test at α = 5 and based on the average oil content of 4 control plants.

REFERENCES

Becker, D., Kemper, E., Schell, J., and Masterson, R. (1993) Plant Mol Biol. 20, 1195–7

Bell, R. M., and Coleman, R. A. (1983) in The Enzymes (Boyer, P. D., ed.) Vol. 16, pp. 87–111, Academic Press, Orlando Bligh, E. G. and Dyer, W. J. (1959) Can. J. Biochem. Physiol. 37, 911–917

Cao, Y.-Z., and Huang, A. H. C. (1986) Plant. Physiol. 82, 813–820

Cases, S., Smith, S. J., Zheng, Y.-W., Myers, H. M., Lear, S. R., Sande, E., Novak, S., Collins, C., Welch, C. B., Lusis, A. J., Erickson, S. K., and Farese, R. V. (1998) Proc. Natl. Sci. 95, 13018–13023

Dahlqvist, A., Ståhl, U., Lenman, M., Banas, A., Ronne, H., and Stymne, S. (1999) Enzymes catalysing a transacylation reaction involved in triacylglycerol synthesis. Presented at Biochem, Mol. Biol. Plant Fatty Acids Glycerolipids Symp., South Lake Tahoe, Calif., USA Dahlqvist, A., Ståhl, U., Lenman, M., Banas, A., Lee, M., Sandager, L., Ronne, H., and Stymne, S. (2000) Proc. Natl. Acad. Sci. USA. 97, 6487–6492

Ekundayo, R. O. and Packter, N. M. (1994) Microbiology 140, 931–943

Hobbs, D. H., Lu, C., and Hills, M. J. (1999) FEBS Letters 452, 145–149

Lardizabal K. D., Hawkins D., Thompson G. A. (2000) International Patent No. WO 00/01713

Lardizabal, K., Hawkins, D., Mai, J., and Wagner, N. (1999) Identification of a new diacylglycerol acyltransferase gene family. Presented at Biochem, Mol. Biol. Plant Fatty Acids Glycerolipids Symp., South Lake Tahoe, Calif. USA Lassner, M. W., Ruezinsky, D. M. (1999) International patent No. WO 99/63096

Martin, B. A. and Wilson, R. F. (1983) Lipids 18, 1–6

Meesters, P. A. E. P., Huijberts, G. N. M., and Eggink, G. (1996) Appl. Microbiol. Biotechnol. 45, 575–579

Oelkers, P., Behari, A., Cromley, D., Billheimer, J. T., and Sturley, S. I., (1998) J. Biol. Chem. 273, 26765–26771

Ratledge, C. (1989) in *Microbiol Lipids* (Ratledge, C. and Wilkinson, S. G., eds.) 2, 567–668, Academic Press, London Ronne, H., Carlberg, J., Hu, G.-Z., and Nehlin, J. O. (1991) *Mol. Cell. Biol.* 11, 4876–4884

Sherman, F., Fink, G. R., and Hicks, J. B. (1986) Laboratory Course Manual for Methods in Yeast Genetics, Cold Spring Harbor Lab. Press, Plainview, N.Y.

Stålberg, K., Ellerström, M., Josefsson, L. G., and Rask, L. (1993) *Plant Mol Biol.* 23, 671–83

Ståhl, U. (1999) *Phospholipases and transacylases involved in triacylglycerol synthesis.* Presented at 23rd World Congress and Exhibition of the International Society for Fat Research (ISF), Brighton, UK Thomas, B. J., and Rothstein, R. (1989) *Cell* 56, 619–630

Valvekens, D., van Lijsebettens, M., and van Montagu, M. (1992) in *Plant Tissue Culture* (Lindsey K.), Kluwer Academic Publishers, NL Yang, H., Bard, M., Bruner, D. A., Gleeson, A., Deckelbaum, R. J., Aljinovic, G., Pohl, T. M., Rothstein, R., and Sturley, S. L. (1996) *Science* 272, 1353–1356

Yu, C., Kennedy, N. J., Chang, C. Y. G., and Rothblatt, J. A. (1996) *J. Biol. Chem.* 271, 24157–24163

---

What is claimed is:

1. A method for increasing the oil content of an oil-producing plant, comprising:
    transforming said plant with a nucleotide sequence so that said plant expresses an enzyme that catalyzes the transfer of a fatty acid from acyl-CoA to diacylglycerol for the production of triacylglycerol (TAG), wherein said enzyme comprises SEQ ID NO. 2, and wherein the oil content of said plant has been increased relative to a plant that has not been transformed.

2. The method according to claim 1, wherein said nucleotide sequence comprises SEQ ID NO. 1.

3. The method according to claim 1, wherein said nucleotide sequence is from a *Saccharomyces cerevisiae* ARE1 gene.

4. An isolated nucleotide sequence encoding for an enzyme that catalyzes the transfer of a fatty acid from acyl-CoA to diacylglycerol for the production of triacylglycerol (TAG), wherein said nucleotide sequence encodes an enzyme having an amino acid sequence comprising SEQ ID NO. 2.

5. A transgenic plant, comprising a plasmid or genome containing the nucleotide sequence according to claim 4, wherein said nucleotide sequence is transferred by recombinant DNA technology.

6. The transgenic plant according to claim 5, wherein said plant is selected from agricultural plants.

7. The transgenic plant according to claim 6, wherein said plant is an oil seed crop.

8. The transgenic plant according to claim 7, wherein said nucleotide sequence is expressed under the control of a storage organ specific promoter.

9. The transgenic plant according to claim 8, wherein said nucleotide sequence is expressed under control of a seed-specific promoter.

10. A method for increasing the oil content of an oil-producing organism, comprising:

transforming said organism selected from the group consisting of Arabidopsis and yeast with a nucleotide sequence comprising SEQ. ID NO. 1 or ARE1 gene so that said organism expresses an enzyme and catalyzes the transfer of a fatty acid from acyl-CoA to diacylglycerol for the production of triacylglycerol (TAG), said enzyme comprising an amino acid sequence of SEQ ID NO. 2, and wherein the oil content of said organism has been increased relative to an organism that has not been transformed.

11. A method for increasing the oil content of an oil-producing plant, comprising:

transforming said plant with a nucleotide sequence comprising SEQ ID NO. 1 or ARE1 gene so that said plant expresses an enzyme and catalyzes the transfer of a fatty acid from acyl-CoA to diacylglycerol for the production of triacylglycerol (TAG), said enzyme comprising an amino acid sequence of SEQ ID NO. 2, and wherein the oil content of said plant has been increased relative to a plant that has not been transformed.

* * * * *